(12) United States Patent
Speziali et al.

(10) Patent No.: US 7,854,762 B2
(45) Date of Patent: Dec. 21, 2010

(54) DEVICES AND METHODS FOR REDUCING CARDIAC VALVE REGURGITATION

(75) Inventors: Giovanni Speziali, Pittsburgh, PA (US); Charles Bruce, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 271 days.

(21) Appl. No.: 11/920,670

(22) PCT Filed: May 22, 2006

(86) PCT No.: PCT/US2006/019554

§ 371 (c)(1),
(2), (4) Date: Apr. 9, 2008

(87) PCT Pub. No.: WO2006/127509

PCT Pub. Date: Nov. 30, 2006

(65) Prior Publication Data

US 2009/0131880 A1      May 21, 2009

Related U.S. Application Data

(60) Provisional application No. 60/683,089, filed on May 20, 2005.

(51) Int. Cl.
*A61F 2/24* (2006.01)
(52) U.S. Cl. .................................................. 623/2.11
(58) Field of Classification Search ......... 623/2.1–2.11; 600/16, 37
See application file for complete search history.

(56) References Cited

U.S. PATENT DOCUMENTS

| | | | |
|---|---|---|---|
| 4,422,447 A | 12/1983 | Schiff | |
| 5,338,301 A | 8/1994 | Diaz | |
| 5,350,419 A | 9/1994 | Bendel et al. | |
| 5,509,428 A | 4/1996 | Dunlop | |
| 6,010,479 A | 1/2000 | Dimitri | |
| 6,482,228 B1 | 11/2002 | Norred | |
| 6,743,208 B1 * | 6/2004 | Coyle | 604/164.13 |
| 6,764,510 B2 | 7/2004 | Vidlund et al. | |
| 6,896,690 B1 * | 5/2005 | Lambrecht et al. | 606/200 |
| 2006/0199995 A1 * | 9/2006 | Vijay | 600/37 |
| 2008/0177130 A1 * | 7/2008 | Vijay | 600/16 |
| 2009/0030510 A1 * | 1/2009 | Ho | 623/2.11 |
| 2009/0254114 A1 * | 10/2009 | Hirszowicz et al. | 606/194 |
| 2009/0299327 A1 * | 12/2009 | Tilson et al. | 604/500 |
| 2010/0042208 A1 * | 2/2010 | Herrmann et al. | 623/2.11 |
| 2010/0057201 A1 * | 3/2010 | Flagle et al. | 623/2.16 |
| 2010/0076548 A1 * | 3/2010 | Konno | 623/2.1 |

OTHER PUBLICATIONS

U.S. Appl. No. 60/683,089, filed May 20, 2005, Speziali et al.

* cited by examiner

*Primary Examiner*—Suzette J Gherbi
(74) *Attorney, Agent, or Firm*—Mueting, Raasch & Gebhardt, P.A.

(57) ABSTRACT

Devices and methods that may be used to reduce valve regurgitation are disclosed by locating a body across the regurgitant valve. When the valve closes, the body obliterates/ameliorates the regurgitant orifice in the valve, thereby reducing or preventing valve regurgitation. The body may be expandable. The devices may be implantable such that they can remain in place within a subject for extended periods of time.

16 Claims, 3 Drawing Sheets

DEVICES AND METHODS FOR REDUCING CARDIAC VALVE REGURGITATION

RELATED APPLICATION

The present application is a U.S. National Stage Application of International Application No. PCT/US2006/019554, filed May 22, 2006 and titled DEVICES AND METHODS FOR REDUCING CARDIAC VALVE REGURGITATION, which claims the benefit under 35 U.S.C. §119(e) of U.S. Provisional Patent Application No. 60/683,089, filed May 20, 2005, and titled DEVICES AND METHODS FOR REDUCING CARDIAC VALVE REGURGITATION, all of which are hereby incorporated by reference in their entirety.

The present invention relates to devices and methods for reducing cardiac valve regurgitation, more particularly, the present invention provides expandable devices designed to limit flow through a leaking cardiac valve and methods of using those devices.

There are four valves in the human heart. The mitral and tricuspid valves are situated between the left atrium and ventricle and between the right atrium and ventricle respectively. The aortic valve is between the left ventricle and the aorta, and the pulmonary valve is situated between the right ventricle and the pulmonary artery. Heart valves include a fibrous frame (or annulus) and moveable leaflets or cusps.

Valvular regurgitation can occur when the valve leaflets (for the tricuspid and mitral valve) or the valve cusps (for the aortic or pulmonary valve) do not coapt properly when the valve is closed. This can be caused by a variety of disease processes, including, e.g., leaflet or cusp retraction, annular dilatation (e.g., annuloaortic ectasia, mitral or tricuspid annular dilatation, etc.), etc. Also, the leaflets or cusps of a valve can prolapse (or fall back) as a result of stretching or rupture of their support system. What all these processes have in common is that an orifice (a regurgitant orifice) remains after valve closure through which blood can flow backwards (i.e., not in the intended direction), thus creating valve regurgitation.

In some instances, valve regurgitation may be beneficial as discussed in U.S. Pat. No. 5,509,428 (Dunlop). In most instances, however, valve regurgitation is not desirable.

SUMMARY OF THE INVENTION

The present invention provides devices and methods that may be used to reduce valve regurgitation. The devices may preferably be implantable such that they can remain in place within a subject for extended periods of time.

The present invention preferably provides a device with an appropriately sized and shaped body that can be placed across a regurgitant valve so that, when the valve closes, the body obliterates/ameliorates the regurgitant orifice in the valve, thereby reducing or preventing valve regurgitation.

It may be preferred that the shape of the body be such that when the valve closes, the body itself provides support to the valve leaflets or cusps. It is anticipated that in some situations (particularly when regurgitation is functional due to annular dilatation) reverse remodeling of the volume overloaded chamber may occur such that the regurgitation may decrease over time as the annular dilatation recedes permitting reduction in body size or even removal of the body.

In some embodiments, the body may change shape in response to the direction of fluid flow to enhance the ability of the body to reduce or prevent regurgitant flow.

In one aspect, the present invention may provide a device for reducing regurgitant flow through a cardiac valve, wherein the device includes an expandable body, wherein the body has a collapsed profile adapted for percutaneous delivery of the body to an internal body location and an expanded profile larger than the collapsed profile, wherein the body is adapted to close a regurgitant orifice in a cardiac valve when in the expanded profile. The device also includes a tether attached to the body, wherein the tether has a proximal end attached to the body and a distal end distal from the body; and an anchor located at the distal end of the tether, wherein the anchor is adapted to fix the position of the distal end of the tether at a selected location.

In one variation, the devices may include, e.g., an expandable body in the form of an inflatable balloon and an inflation lumen in fluid communication with the inflatable balloon, wherein the inflatable balloon can be expanded to place the expandable body in the expanded profile by delivering an inflation fluid into the inflatable balloon through the inflation lumen. The inflation fluid may include a radio-opaque substance.

In another variation, the expandable body may include a supporting structure and a sheet material attached to the supporting structure. The sheet material may include a polymeric film.

The expandable bodies in devices of the present invention may be constructed of fluid-impermeable materials.

The expandable bodies in devices of the present invention may have a dynamic hemodynamic conformational shape that changes in response to fluid flow and/or pressure variations around the expandable body.

The location of the expandable body on the tether may be, in some embodiments, adjusted.

The cross-sectional profile of the expandable bodies in devices of the present invention may be selected from the group consisting of round, oval, flattened oval, triangular, fluted, and combinations of two or more thereof.

In another aspect, the present invention may provide a method of reducing regurgitant flow through a cardiac valve by providing a device that includes an expandable body, wherein the body has a collapsed profile adapted for percutaneous delivery of the body to an internal body location and an expanded profile larger than the collapsed profile, wherein the body is adapted to close a regurgitant orifice in a cardiac valve when in the expanded profile; a tether attached to the body, wherein the tether has a proximal end attached to the body and a distal end distal from the body; and an anchor located at the distal end of the tether. The method further includes delivering the device to an internal body location; attaching the anchor to tissue at a selected location, wherein the expandable body is located across a regurgitant cardiac valve; and expanding the expandable body from its collapsed profile to its expanded profile.

The methods of the present invention may optionally include expanding the expandable body by inflating a balloon located within the expandable body. The inflating may include delivering an inflation fluid to the expandable body, wherein the inflation fluid may include a radio-opaque substance.

The expandable body may include a supporting structure and a sheet material attached to the supporting structure, wherein expanding the expandable body may include expanding the supporting structure. The sheet material may include a polymeric film.

The expandable bodies used in the methods of the present invention may be constructed of fluid-impermeable materials.

The expandable bodies used in the methods of the present invention may have a dynamic hemodynamic conformational shape that changes in response to fluid flow and/or pressure variations around the expandable body.

The methods of the present invention may optionally include adjusting a location of the expandable body on the tether after attaching the anchor.

The cross-sectional profile of the expandable body used in a method of the present invention may be selected from the group consisting of round, oval, flattened oval, triangular, fluted, and combinations of two or more thereof.

The methods of the present invention may include selecting the expandable body to correlate with the shape of a regurgitant orifice in the regurgitant valve.

These and other features and advantages of the devices and methods of the present invention may be described below in connection with various exemplary embodiments of the invention.

BRIEF DESCRIPTIONS OF THE FIGURES

DESCRIPTION OF EXEMPLARY EMBODIMENTS OF THE INVENTION

In the following detailed description of some exemplary embodiments of the invention, reference is made to the accompanying figures which form a part hereof, and in which are shown, by way of illustration, specific embodiments in which the invention may be practiced. It is to be understood that other embodiments may be utilized and structural changes may be made without departing from the scope of the present invention.

Figure 1:
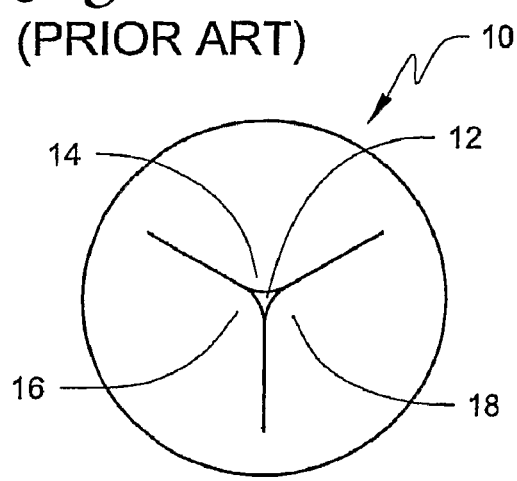
FIG. 1 depicts a competent tricuspid valve when closed.
Figure 2:
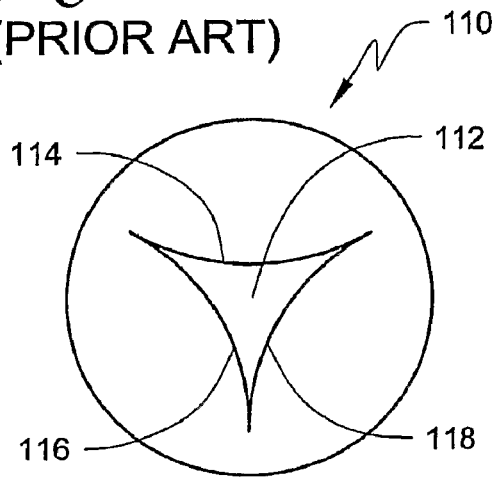
FIG. 2 depicts a tricuspid valve with a regurgitant orifice.

FIGS. 1 & 2 depict tricuspid valves, with the valve 10 in FIG. 1 being a competent valve in the closed position in which the valve 10 essentially prevents backflow with leaflets or cusps 14, 16 & 18 that act together to close the opening 12.

In contrast, FIG. 2 depicts a tricuspid valve 110 that includes a regurgitant orifice 112 that is not closed by the leaflets or cusps 114, 116 & 118. Backflow through the regurgitant orifice 112 in the valve 110 may, however, be reduced using the devices and methods of the present invention.

Figure 3:
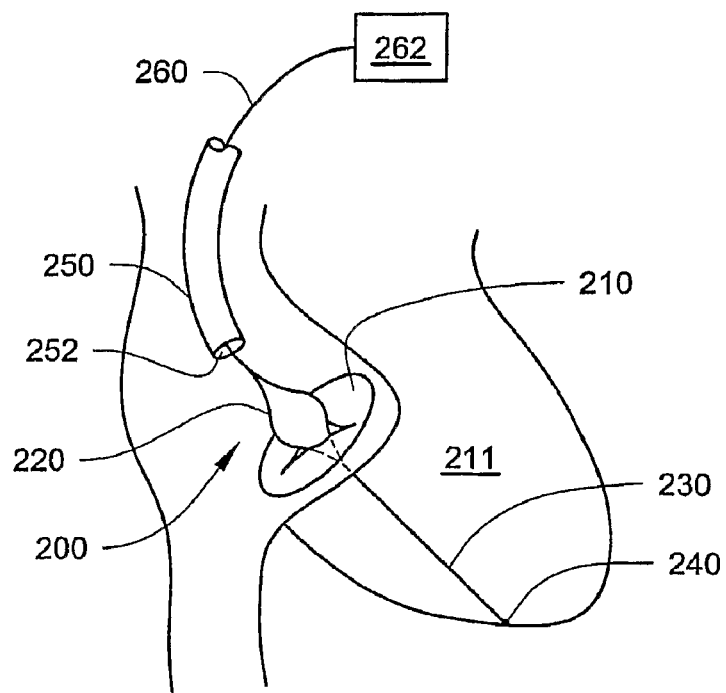
FIG. 3 depicts one example of a device for reducing regurgitant flow through a tricuspid valve, the device being deployed within a right ventricle.
Figure 4:
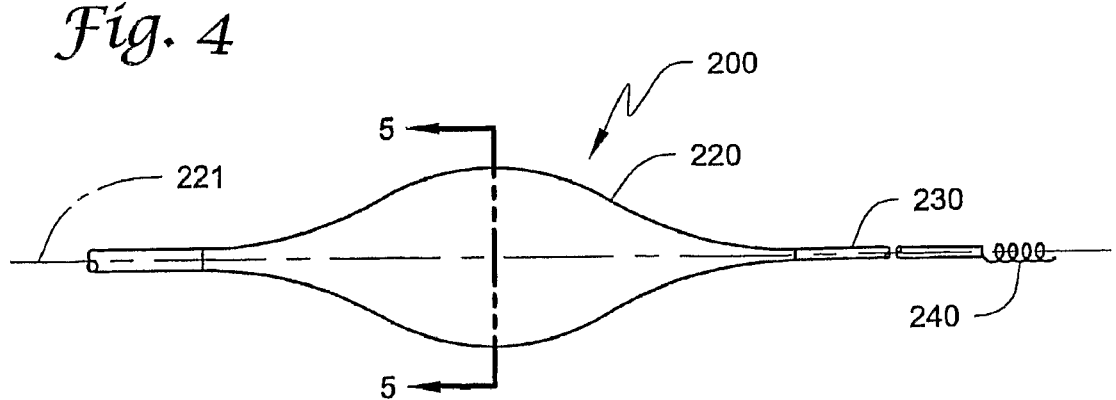
FIG. 4 is a side view of the device of FIG. 3 before deployment.

FIG. 3 depicts deployment of one exemplary device in a heart while FIG. 4 depicts the distal portion of the device 200 outside of the heart. The device 200 includes a body 220 that is positioned across a regurgitant valve 210. The body 220 is retained in place by a tether 230 that is connected to tissue using an anchor 240 attached to the wall of the light ventricle 211.

Although the device 200 is depicted as deployed within the right ventricle 211, it should be understood that the devices of the present could alternatively include a body positioned across an aortic valve and attached using a tether anchored within the left ventricle.

Deployment of the device may preferably be accomplished percutaneously, using a catheter 250 having a lumen 252 through which the device is delivered and deployed. After deployment, the catheter 250 may preferably be removed, leaving the body 220 in position across the regurgitant valve 210. The device 200 may preferably be inserted through a peripheral vein or artery using delivery catheter 250. Alternatively, the device 200 may be positioned through a surgical procedure directly through the heart muscle into the appropriate heart cavity. If the body 220 of the device 200 is in the form of an expandable body (e.g., inflatable balloon, etc.) that can be delivered in a smaller, unexpanded state, it may be more suited for delivery through a peripheral vein or artery.

It may be preferred that the body 220 placed across the valve 210 be liquid impermeable, i.e., that blood cannot flow through the body 220 itself. In some instances, limited permeability of the body 220 may be acceptable where the permeability is low enough such that the body 220 substantially closes the regurgitant orifice such that biologically insignificant amounts of blood pass therethrough when the valve 210 is closed with the body 220 in position across the valve 210.

The body 220 may preferably be retained in place across the valve 210 using, e.g., a temporarily or permanently implanted tether 230 whose extremities can be secured to the heart and/or to a blood vessel in such a way to prevent dislodgement or migration of the body 220 from the valve 210. The tether 230 may take any suitable form, e.g., the tether 230 may be a modified catheter, etc. The body 220, tether 230, anchor 240 are depicted in FIG. 4 as extending along a longitudinal axis 221. It may be preferred that the tether 230 hold the body in position under both tension and (at least to some extent) compression acting along the longitudinal axis 221.

The body 220 may be attached such that its position across the valve 210 may be adjusted after implantation. For example, it may be preferred that, if the body 220 is affixed using a tether 230 anchored within the subject, the body 220 may preferably be movable proximally or distally along the tether 230 to adjust its location across the valve 210.

One example of a potentially useful tether 230 may be in the form of a ventricular pacemaker lead to which the body 220 is attached. When in place across the valve 210, the body 220 can be used to treat tricuspid valve regurgitation. The distal end of the tether (lead) 230 may preferably be secured to the right ventricular endocardial surface using, e.g., a tissue anchor 240, such that the lead acts as a tether 230 to retain the body 220 in position across the valve 210.

The tether 230 may be attached by any suitable technique or techniques. Some potentially suitable attachment techniques may involve, e.g., screws or other structures commonly used in the field of cardiac pacemaker/defibrillation leads. See, e.g., U.S. Pat. No. 5,350,419 (Bendel et al.). The structures used to deliver the body 220 may preferably be flexible, semi-flexible and/or steerable. Alternatively or in addition to the screws or other structures used in connection with pacemaker/defibrillation leads, the body 220 may be held in place by one or more sutures, strings, wires, etc. appropriately anchored to the subject's heart chambers and/or vessels.

It may be preferred that the body 220 be provided in the form an expandable structure such as, e.g., an expandable balloon. The expandable body 220 may be characterized as having a collapsed profile adapted for percutaneous delivery of the body 220 (through, e.g., catheter 250) to an internal body location and an expanded profile larger than the collapsed profile, wherein the expandable body 220 is adapted to close a regurgitant orifice in a cardiac valve when in the expanded profile.

If the body 220 is provided in the form of a balloon, it may be preferred that the balloon be manufactured of a soft, pliable material or polymer (e.g., polyethylene, polyurethane, etc.) and that can be inflated or deflated as needed to precisely obliterate the regurgitant orifice. Examples of some potentially suitable polymers found in other medical balloons/materials may be described in, e.g., U.S. Pat. No. 4,422,447 (Schiff); U.S. Pat. No. 5,338,301 (Diaz); or U.S. Pat. No. 6,010,479 (Dimitri).

If the body 220 is in the form of an inflatable balloon, a catheter 260 (e.g., the same catheter used to deliver and/or secure the balloon in position or a different catheter), may be used to connect the body 220 to an inflation source 262. Using the catheter 262, inflation fluid may be delivered to the body 220 through a port such that balloon inflation can be adjusted as needed. Inflatable balloons used in connection with the present invention may be filled with any suitable gas, liquid, gel, etc. Examples of some potentially suitable materials may include, e.g., saline solution, $CO_2$, etc.

The body, tether, anchor, etc. and/or inflation fluid used to inflate the body (if any) may preferably include a radio-opaque substance or markers to check its correct positioning, continued inflation, leakage, etc.

In some embodiments, the inflation source 262 may remain connected to the body 220 (through, e.g., catheter 260 or another catheter). The inflation source 262 could then synchronize inflation and deflation of the body 220 to coincide with valve 210 closing and opening. The inflation source 262 may preferably inject a fluid to inflate and, e.g., remove the inflation fluid from the body 220 (partially or completely) during deflation via, e.g., a pump and reservoir contained in inflation source 220. In some instances, the entire system, e.g., body 220, catheter 260, and inflation source 262 may all be implantable within a subject.

The bodies used in connection with the present invention may have, e.g., a round cross-section. Body 220, as depicted in the cross-sectional view of FIG. 5, has a round cross-sectional shape formed by wall 222 and internal volume 224. Also seen in FIG. 5 is a port 226 through which inflation fluid may be delivered and/or removed from the internal volume 224 of the body 220.

Figure 5:
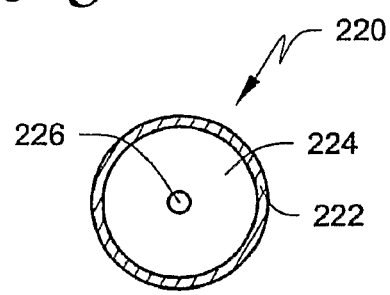
FIG. 5 is a cross-sectional view of the device of FIG. 4 taken along line 5-5 in FIG. 4.
Figure 6:
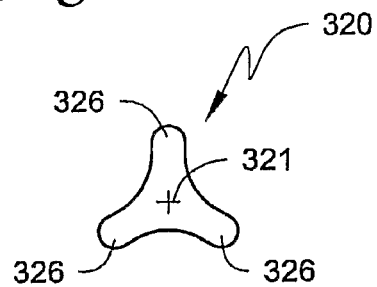
FIG. 6 is a cross-sectional view of an alternative embodiment of an expandable body that may be used in devices according to the present invention.

Although body 220 has a generally circular profile or cross-section as seen in FIG. 5, the bodies used to close regurgitant valve orifices in accordance with the present invention may have a cross-section that more closely conforms to the shape of the regurgitant orifice (e.g., oval, triangular, flattened oval, fluted, combinations or two or more thereof, etc.). FIG. 6 is a cross-sectional view of only one potential example of a body 320 that includes three flutes 326 extending radially outward from the longitudinal axis 321.

In some instances, the shape or profile of the body used to occupy a regurgitant orifice may preferably be selected from a variety of shapes and/or sizes (or even custom tailored to each application) by obtaining an image of the regurgitant orifice to use as a guide or template to select/build an appropriate-shaped body. The longitudinal section of the body (i.e., the shape along the longitudinal axis) may preferably be in the shape of a fusiform or other appropriate shape that reduces flow obstruction past the body when the valve is in the open position.

As discussed above, the bodies used in connection with the present invention may take a variety of cross-sectional shapes, e.g., round, oval, etc. If the body is in the form of an inflatable balloon, the balloon may preferably exhibit some compliance and flexibility that may help to more closely conform to the shape of the regurgitant orifice during closing. In some instances, the balloon may preferably include an internal rigid or semi-rigid structure (e.g., fine metal wire ribbing) to assist in maintaining a selected shape of the balloon. Such structures may also allow for fine-tuning of the balloon shape after implantation by deforming the structures with the body deployed in the valve.

Such structures in the body may also be used to expand the body to a usable cross-sectional profile in the absence of an inflation fluid (e.g., such structures could be manufactured of shape memory materials such as, e.g., nickel-titanium alloys, shape memory polymers, etc.).

Although some of the bodies used to close regurgitant orifices may be static, i.e., may have a fixed shape after deployment (and expansion, if required), other bodies used in devices of the present invention may alternatively change shape in response to fluid flow past the body. Such changeable bodies may be characterized as having a dynamic hemodynamic conformational shape. Conformational change may allow the body to adopt an improved hemodynamic profile in diastole while increasing obstruction to regurgitant flow and leaflet support in systole.

Figure 7A:
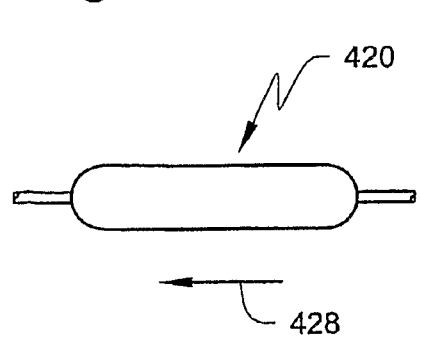
FIGS. 7A & 7B depict one example of a body that may be used with a device of the present invention, the body being capable of dynamically changing shape in response to changes in the direction of fluid flow.
Figure 7B:
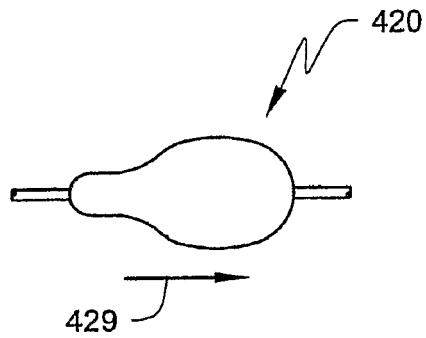

FIGS. 7A & 7B depict an example of one such body 420 which, when subjected to fluid flow in the direction of arrow 428, the body 420 may take a shape in which the proximal and distal ends have a similar size (e.g., a more cylindrical or sausage-like shape) such that flow past the body 420 in the direction 428 is facilitated. In contrast, during reverse flow in the direction of arrow 429 in FIG. 7B, the body 420 may assume a shape that is more capable of restricting the regurgitant orifice. For example, the body 420 may assume a pear-like shape in which the cross-sectional size of the balloon is enlarged at the downstream end of the body 420 (e.g., due to increased ventricular pressure as compared with the lower atrial pressure). This dynamic hemodynamic conformational change may preferably increase the body diameter in relation to the regurgitant orifice and, in addition, the sides of the pear-shaped body may provide increased support for the leaflets of a valve traversed by the body 420.

Figure 8:
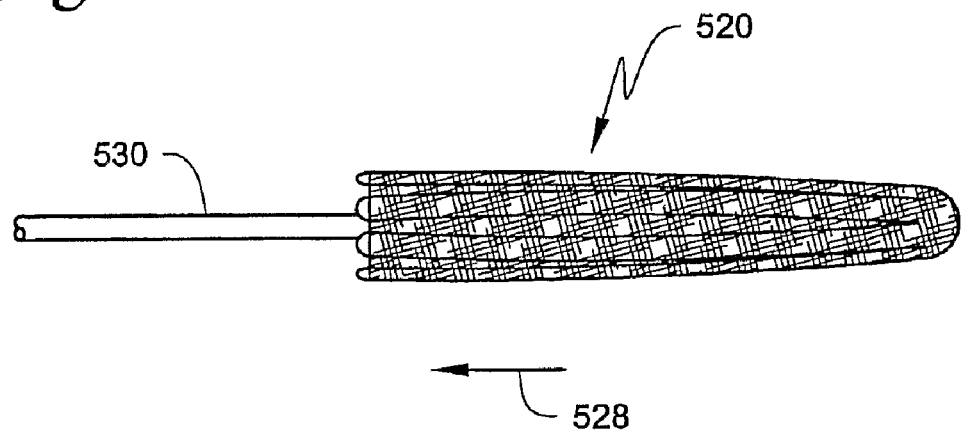
FIGS. 8 & 9 depict another example of a device for reducing regurgitant flow, the device assuming a smaller profile during flow in the intended direction (FIG. 8) and a larger profile in response to backward flow (FIG. 9).
Figure 9:
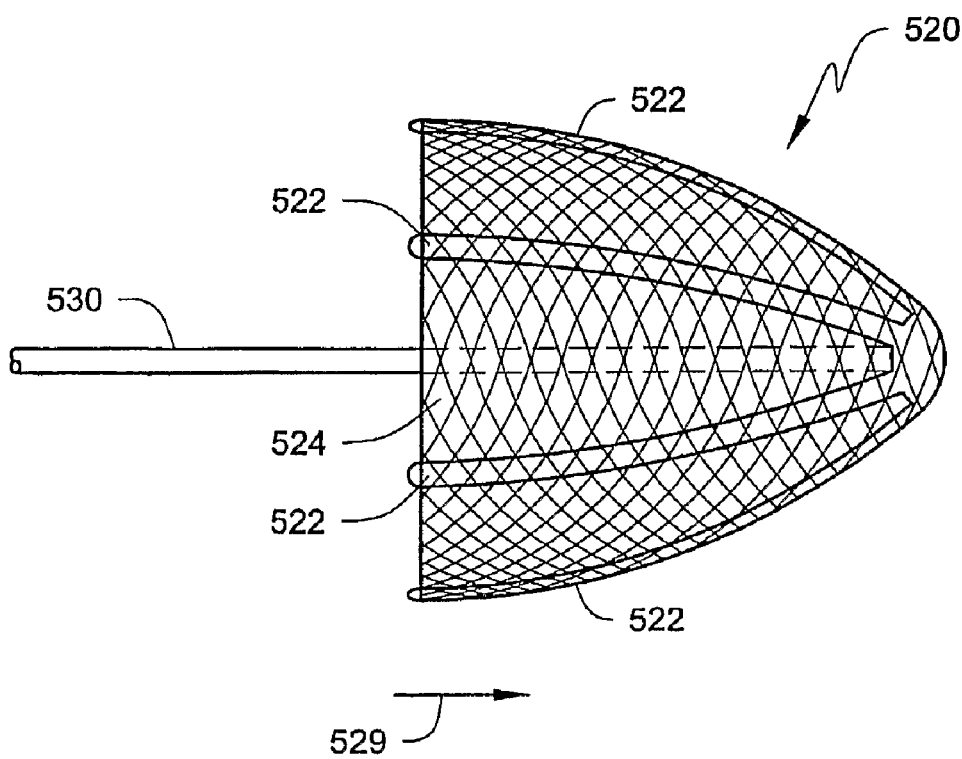

Still another example of a device with a potentially suitable body that may be used in connection with the present invention to reduce regurgitant flow through a valve is depicted in FIGS. 8 & 9. The body 520 is preferably, like the devices described above, preferably connected to a tether 530 (only a portion of which is depicted) or otherwise attached such that the body 520 can be held in place relative to a regurgitant valve. The tether 530 and body 520 may preferably be delivered and attached in much the same manner with the other devices described herein.

In general, the body 520 may be described as having an umbrella-like or parachute-like shape. It may be preferred that the body 520 have a retained memory structure biased to hold the body 520 in its open shape (FIG. 9). To accomplish that, it may be preferred to manufacture the body 520 with arms or struts 522 constructed of, e.g., shape-memory material (e.g., nickel-titanium alloys, shape-memory polymers, etc.). Flow past the body 529 in the direction of arrow 529 in FIG. 9 may be restricted by suspending sheet material 524 between the arms 522. The sheet material 524 may be constructed of any suitable material, e.g., polymer films (e.g., polyethylene, etc.), meshes, fabrics, etc. may all be used if they provide a desired level of flow restriction.

During, e.g., diastole, the pressure of inflowing fluid would preferably collapse the arms 522 sufficiently to allow blood to flow past the body 520 in the direction of arrow 528 in FIG. 8. During, e.g., systole, the arms 522 would preferably regain their expanded shape to reduce regurgitation in the direction of the arrow 529 as seen in FIG. 9. As a result, the body 520 may also be characterized as having a dynamic hemodynamic conformational shape. It may be preferred that the valve leaflets of a valve with which the device is used contact the body 520 when it is in its expanded state as seen in FIG. 9, with the body potentially providing support to the leaflets.

Although not explicitly depicted in connection with any specific exemplary embodiments, the devices of the present invention may include pressure sensors or other sensors capable of transmitting hemodynamic or other information outside the subject. Such sensors may be located on or in the body, the tether, or any other selected location on or in the device.

As used herein and in the appended claims, the singular forms "a," "and," and "the" include plural referents unless explicitly limited to the singular form or the context clearly dictates otherwise.

All references and publications cited herein are expressly incorporated herein by reference in their entirety into this disclosure. Illustrative embodiments of this invention are discussed and reference has been made to possible variations within the scope of this invention. These and other variations and modifications in the invention will be apparent to those skilled in the art without departing from the scope of the invention, and it should be understood that this invention is not limited to the illustrative embodiments set forth herein. Accordingly, the invention is to be limited only by the claims provided below and equivalents thereof.

The invention claimed is:

1. A device for reducing regurgitant flow through a cardiac valve, the device comprising:
   an expandable body, wherein the body comprises a collapsed profile adapted for percutaneous delivery of the body to an internal body location and an expanded profile larger than the collapsed profile;
   a tether attached to the body; and
   an anchor located at the distal end of the tether, wherein the anchor is adapted to fix the position of a distal end of the tether at a selected location;
   wherein the tether comprises a length between the anchor and the body such that the body is positioned across the cardiac valve when the device is deployed in a heart.

2. A device according to claim 1, wherein the expandable body comprises an inflatable balloon, and wherein the device further comprises an inflation lumen in fluid communication with the inflatable balloon, wherein the inflatable balloon can be expanded to place the expandable body in the expanded profile by delivering an inflation fluid into the inflatable balloon through the inflation lumen.

3. A device according to claim 2, wherein the inflation fluid comprises a radio-opaque substance.

4. A device according to claim 1, wherein the expandable body comprises a supporting structure and a sheet material attached to the supporting structure.

5. A device according to claim 4, wherein the sheet material comprises a polymeric film.

6. A device according to claim 1, wherein the expandable body is constructed of fluid-impermeable materials.

7. A device according to claim 1, wherein the expandable body comprises a dynamic hemodynamic conformational shape that changes in response to fluid flow and/or pressure variations around the expandable body.

8. A device according to claim 1, wherein a location of the expandable body on the tether can be adjusted.

9. A device according to claim 1, wherein the cross-sectional profile of the expandable body is selected from the group consisting of round, oval, flattened oval, triangular, fluted, and combinations of two or more thereof.

10. A device for reducing regurgitant flow through a cardiac valve, the device comprising:
    an expandable body in the form of an inflatable balloon, wherein the expandable body comprises a collapsed profile adapted for percutaneous delivery of the expandable body to an internal body location and an expanded profile larger than the collapsed profile;
    an inflation lumen in fluid communication with the inflatable balloon, wherein the inflatable balloon can be expanded to place the expandable body in the expanded profile by delivering an inflation fluid into the inflatable balloon through the inflation lumen;
    a tether attached to the expandable body, wherein a location of the expandable body on the tether can be adjusted; and
    an anchor located at the distal end of the tether, wherein the anchor is adapted to fix the position of a distal end of the tether at a selected location;
    wherein the tether comprises a length between the anchor and the body such that the body is positioned across the cardiac valve when the device is deployed in a heart.

11. A device according to claim 1, wherein the body is adapted to close a regurgitant orifice in the cardiac valve when in the expanded profile.

12. A device according to claim 1, wherein the tether comprises a proximal end attached to the body and a distal end distal from the body.

13. A device according to claim 1, wherein the expandable body positioned across the cardiac valve comprises a round cross-sectional profile.

14. A device according to claim 1, wherein the expandable body positioned across the cardiac valve comprises a flattened oval cross-sectional profile.

15. A device according to claim 1, wherein the expandable body positioned across the cardiac valve comprises a triangular cross-sectional profile.

16. A device according to claim 1, wherein the expandable body positioned across the cardiac valve comprises a fluted cross-sectional profile.

* * * * *